(12) United States Patent
Ralph et al.

(10) Patent No.: US 7,604,664 B2
(45) Date of Patent: *Oct. 20, 2009

(54) SPINAL BASEPLATES WITH BALL JOINT COUPLING AND A RETAINING MEMBER

(75) Inventors: James D. Ralph, Seaside Park, NJ (US); Stephen Tatar, Montville, NJ (US)

(73) Assignee: SpineCore, Inc., Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/151,280

(22) Filed: May 20, 2002

(65) Prior Publication Data

US 2003/0069643 A1 Apr. 10, 2003

Related U.S. Application Data

(63) Continuation-in-part of application No. 10/140,153, filed on May 7, 2002, now abandoned, which is a continuation-in-part of application No. 09/970,479, filed on Oct. 4, 2001, now Pat. No. 6,669,730, which is a continuation-in-part of application No. 09/968,046, filed on Oct. 1, 2001, now abandoned, said application No. 10/140,153 is a continuation-in-part of application No. 10/128,619, filed on Apr. 23, 2002, now Pat. No. 6,863,689, and a continuation-in-part of application No. 09/982,148, filed on Oct. 18, 2001, now Pat. No. 6,673,113, which is a continuation-in-part of application No. 09/906,119, filed on Jul. 16, 2001, now Pat. No. 6,607,559.

(51) Int. Cl.
*A61F 2/44* (2006.01)

(52) U.S. Cl. ............... 623/17.14; 623/17.13; 623/17.15

(58) Field of Classification Search .............. 623/17.13, 623/17.14, 17.15, 17.16, 17.11, 17.12
See application file for complete search history.

(56) References Cited

U.S. PATENT DOCUMENTS

| | | | |
|---|---|---|---|
| 2,193,122 A * | 3/1940 | Crabbs ...................... 411/900 |
| 3,867,728 A | 2/1975 | Stubstad et al. |
| 4,309,777 A | 1/1982 | Patil |
| 4,605,417 A | 8/1986 | Fleischauer |
| 4,759,766 A | 7/1988 | Buettner-Janz et al. |
| 4,759,769 A | 7/1988 | Hedman et al. |
| 4,932,969 A | 6/1990 | Frey et al. |
| 4,997,432 A | 3/1991 | Keller |
| 5,112,178 A * | 5/1992 | Overhues et al. ............ 411/544 |

(Continued)

*Primary Examiner*—Brian E. Pellegrino
(74) *Attorney, Agent, or Firm*—Lerner, David, Littenberg, Krumholz & Mentlik, LLP

(57) ABSTRACT

An artificial intervertebral disc having a pair of opposing plate members for seating against opposing vertebral bone surfaces, separated by a spring mechanism. The preferred spring mechanism is at least one spirally slotted belleville washer having radially extending grooves. One plate member has a centrally located ball-shaped protrusion that is rotatably coupled in a central socket in the narrow end of the belleville washer, and the wide end of the belleville washer is held against the other plate member by a shield with rivets. Therefore, the disc assembly will not come apart under tension loads applied to the plate members, and the location of the ball joint coupling provides the disc assembly with a centroid of motion that is centrally located between the vertebral bone surfaces, both causing the disc assembly to behave similarly in these respects to a healthy natural intervertebral disc.

9 Claims, 7 Drawing Sheets

U.S. PATENT DOCUMENTS

| | | | |
|---|---|---|---|
| 5,122,130 | A | 6/1992 | Keller |
| 5,236,460 | A | 8/1993 | Barber |
| 5,258,007 | A | 11/1993 | Spetzler et al. |
| 5,314,477 | A | 5/1994 | Marnay |
| 5,370,697 | A | 12/1994 | Baumgartner |
| 5,401,269 | A | 3/1995 | Buttner-Janz et al. |
| 5,425,773 | A | 6/1995 | Boyd et al. |
| 5,458,642 | A | 10/1995 | Beer et al. |
| 5,507,816 | A | 4/1996 | Bullivant |
| 5,556,431 | A | 9/1996 | Buttner-Janz |
| 5,562,738 | A | 10/1996 | Boyd et al. |
| 5,674,296 | A | 10/1997 | Bryan et al. |
| 5,676,701 | A | 10/1997 | Yuan et al. |
| 5,676,702 | A | 10/1997 | Ratron |
| 5,683,465 | A | 11/1997 | Shinn et al. |
| 5,755,796 | A | 5/1998 | Ibo et al. |
| 5,782,832 | A | 7/1998 | Larsen et al. |
| 5,827,328 | A | 10/1998 | Buttermann |
| 5,865,846 | A | 2/1999 | Bryan et al. |
| 5,888,226 | A | 3/1999 | Rogozinski |
| 5,893,889 | A * | 4/1999 | Harrington ............... 623/17.16 |
| 5,895,428 | A | 4/1999 | Berry |
| 5,899,941 | A | 5/1999 | Nishijima |
| 5,989,291 | A | 11/1999 | Ralph et al. |
| 6,001,130 | A | 12/1999 | Bryan et al. |
| 6,019,792 | A | 2/2000 | Cauthen |
| 6,039,763 | A | 3/2000 | Shelokov |
| 6,063,121 | A | 5/2000 | Xavier et al. |
| 6,113,637 | A | 9/2000 | Gill et al. |
| 6,136,031 | A | 10/2000 | Middleton |
| 6,146,421 | A | 11/2000 | Gordon et al. |
| 6,156,067 | A | 12/2000 | Bryan et al. |
| 6,179,874 | B1 | 1/2001 | Cauthen |
| 6,228,118 | B1 | 5/2001 | Gordon |
| 6,368,350 | B1 | 4/2002 | Erickson et al. |
| 6,375,682 | B1 | 4/2002 | Fleischmann et al. |
| 6,517,580 | B1 | 2/2003 | Ramadan et al. |
| 6,582,466 | B1 | 6/2003 | Gauchet |
| 6,582,468 | B1 | 6/2003 | Gauchet |
| 6,610,092 | B2 | 8/2003 | Ralph et al. |
| 6,645,249 | B2 | 11/2003 | Ralph et al. |
| 6,673,113 | B2 | 1/2004 | Ralph et al. |
| 6,682,562 | B2 | 1/2004 | Viart et al. |
| 6,706,068 | B2 | 3/2004 | Ferree |
| 6,918,934 | B2 | 7/2005 | Ralph et al. |
| 7,022,139 | B2 | 4/2006 | Errico et al. |
| 7,115,132 | B2 | 10/2006 | Errico et al. |
| 2001/0016773 | A1 | 8/2001 | Serhan et al. |
| 2002/0084562 | A1 * | 7/2002 | Kelsey ...................... 267/166 |
| 2002/0111681 | A1 | 8/2002 | Ralph et al. |
| 2002/0111682 | A1 | 8/2002 | Ralph et al. |
| 2002/0111684 | A1 | 8/2002 | Ralph et al. |
| 2002/0111685 | A1 | 8/2002 | Ralph et al. |
| 2003/0014110 | A1 | 1/2003 | Ralph et al. |
| 2003/0014112 | A1 | 1/2003 | Ralph et al. |
| 2003/0028249 | A1 | 2/2003 | Baccelli et al. |
| 2003/0055503 | A1 | 3/2003 | O'Neil |
| 2003/0060886 | A1 | 3/2003 | Van Hoeck et al. |
| 2003/0065395 | A1 * | 4/2003 | Ralph et al. ............... 623/17.13 |
| 2003/0069586 | A1 | 4/2003 | Errico et al. |
| 2003/0069642 | A1 | 4/2003 | Ralph et al. |
| 2003/0074067 | A1 | 4/2003 | Errico et al. |
| 2003/0078666 | A1 | 4/2003 | Ralph et al. |
| 2003/0149482 | A1 | 8/2003 | Michelson |
| 2003/0191534 | A1 | 10/2003 | Viart et al. |
| 2003/0204260 | A1 | 10/2003 | Ferree |
| 2003/0208271 | A1 | 11/2003 | Kuras |
| 2003/0216810 | A1 * | 11/2003 | Ralph et al. ............... 623/17.14 |
| 2003/0229358 | A1 | 12/2003 | Errico et al. |
| 2003/0233097 | A1 | 12/2003 | Ferree |
| 2003/0233148 | A1 | 12/2003 | Ferree |
| 2004/0002759 | A1 | 1/2004 | Ferree |
| 2004/0002762 | A1 | 1/2004 | Hawkins |
| 2004/0010316 | A1 | 1/2004 | William et al. |
| 2004/0030389 | A1 | 2/2004 | Ferree |
| 2004/0030390 | A1 | 2/2004 | Ferree |
| 2004/0034426 | A1 | 2/2004 | Errico et al. |

* cited by examiner

SPINAL BASEPLATES WITH BALL JOINT COUPLING AND A RETAINING MEMBER

CROSS-REFERENCE TO RELATED APPLICATION

The present application is a continuation-in-part application of both U.S. patent application Ser. No. 09/970,479 (filed Oct. 4, 2001) entitled "Intervertebral Spacer Device Utilizing a Spirally Slotted Belleville Washer Having Radially Extending Grooves" now U.S. Pat. No. 6,669,730 ("the '730 patent") as well as U.S. patent application Ser. No. 10/140,153 (filed May 7, 2002) entitled "Artificial Intervertebral Disc Having a Flexible Wire Mesh Vertebral Body Contact Element" now abandoned, the former being a continuation-in-part application of U.S. patent application Ser. No. 09/963,046 (filed Oct. 1, 2001) entitled "Intervertebral Spacer Device Utilizing a Belleville Washer Having Radially Extending Grooves" now abandoned and the latter being a continuation-in-part application of both the '730 patent (detailed above) as well as U.S. patent application Ser. No. 10/128,619 (filed Apr. 23, 2002) entitled "Intervertebral Spacer Having a Flexible Wire Mesh Vertebral Body Contact Element" now U.S. Pat. No. 6,863,689 ("the '689 patent"), which is a continuation-in-part application of both U.S. patent application Ser. No. 09/906,119 (filed Jul. 16, 2001) and entitled "Trial Intervertebral Distraction Spacers" now U.S. Pat. No. 6,607,559 ("the '559 patent") as well as U.S. patent application Ser. No. 09/982,148 (filed Oct. 18, 2001) and entitled "Intervertebral Spacer Device Having Arch Shaped Spring Elements" now U.S. Pat. No. 6,673,113 ("the '113 patent"). All of the above mentioned applications are hereby incorporated by reference herein in their respective entireties.

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device that supports tension loads and provides a centroid of motion centrally located within the intervertebral space.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art which achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional materials, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer that stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space that does not promote the abnormal distribution of biomechanical stresses on the patient's spine.

It is further an object of the present invention to provide an artificial intervertebral disc that has an endplate attachment device (for attaching the endplates of the artificial intervertebral disc to the vertebral bones between which the disc is implanted) with superior gripping and holding strength upon initial implantation and thereafter, as compared with other artificial intervertebral disc endplate attachment devices.

It is further an object of the present invention to provide an artificial intervertebral disc endplate attachment device that deflects during insertion of the artificial intervertebral disc between vertebral bodies.

It is further an object of the present invention to provide an artificial intervertebral disc endplate attachment device that conforms to the concave surface of a vertebral body upon implantation.

It is further an object of the present invention to provide an artificial disc endplate attachment device that does not restrict the angle at which the artificial intervertebral disc can be implanted.

It is further an object of the present invention to provide an artificial disc that supports tension loads.

It is further an object of the present invention to provide an artificial disc that provides a centroid of motion centrally located within the intervertebral space.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is an artificial intervertebral disc comprising a pair of spaced apart plate members, each with a vertebral body contact surface. Because the artificial intervertebral disc is to be positioned between the facing surfaces of adjacent vertebral bodies, the plate members are arranged in a substantially parallel planar alignment (or slightly offset relative to one another in accordance with proper lordotic angulation) with the vertebral body contact surfaces face away from one another. The plate members are to mate with the vertebral bodies so as to not rotate relative thereto, but rather to permit the spinal segments to axially compress and bend relative to one another in manners that mimic the natural motion of the spinal segment. This natural motion is permitted by the performance of a spring member disposed between the secured plates, and the securing of the plate members to the vertebral bone is achieved through the use of an oval convex metal mesh attached to the exterior surface of each plate member. Each convex metal mesh is secured at its perimeter, by laser welds, to the exterior surface of the respective plate member. While domed in its initial undeflected conformation, the mesh deflects as necessary during insertion of the artificial intervertebral disc between vertebral bodies, and, once the artificial intervertebral disc is seated between the vertebral bodies, the mesh deforms as necessary under anatomical loads to reshape itself to the concave surface of the vertebral endplate. This affords the plate member having the metal mesh substantially superior gripping and holding strength upon initial implantation as compared with other artificial disc products. The convex metal mesh further provides an osteoconductive surface through which the bone may ultimately grow. The mesh is preferably comprised of titanium, but can also be formed from other metals and/or non-metals without departing from the scope of the present invention. Inasmuch as the metal mesh is domed, it does not restrict the angle at which the artificial intervertebral disc can be implanted. It should be understood that while the flexible dome is described as a wire mesh, other meshed or solid flexible elements can also be used, including flexible elements comprises of non-metals and/or other metals. Further, the flexibility, deflectability and/or deformability need not be provided by a flexible material, but can alternatively be provided mechanically or by other means.

To enhance the securing of the plate members to the vertebral bones, each plate member further comprises at least a lateral ring of porous coating (which may be a sprayed deposition layer, or an adhesive applied beaded metal layer, or other suitable porous coatings known in the art). This porous ring permits the long-term ingrowth of vertebral bone into the plate member, thus permanently securing the prosthesis within the intervertebral space. It shall be understood that this porous layer may extend beneath the domed metal mesh as well, but is more importantly applied to the lateral rim of the exterior surface of the plate member that seats directly against the vertebral body.

The spring mechanism disposed between the plate members provides a strong restoring force when a compressive load is applied to the plates, and also permits rotation and angulation of the two plates relative to one another. While a wide variety of embodiments are contemplated, a preferred embodiment of the spring mechanism includes a belleville washer utilized as the restoring force providing element, the belleville washer being spirally slotted and having radially extending grooves. In general, the belleville washer is one of the strongest configurations for a spring, and is highly suitable for use as a restoring force providing subassembly for use in an intervertebral spacer element which must endure considerable cyclical loading in an active human adult.

Belleville washers are washers that are generally bowed in the radial direction. Specifically, they have a radial convexity (i.e., the height of the washer is not linearly related to the radial distance, but may, for example, be parabolic in shape). The restoring force of a belleville washer is proportional to the elastic properties of the material. In addition, the magnitude of the compressive load support and the restoring force provided by the belleville washer may be modified by providing slots and/or grooves in the washer. The belleville washer utilized as the force restoring member in the illustrated embodiment is spirally slotted, with the slots initiating on the periphery of the washer and extending along arcs which are generally radially inwardly directed a distance toward the center of the bowed disc, and has radially extending grooves that decrease in width and depth from the outside edge of the washer toward the center of the washer.

As a compressive load is applied to a belleville washer, the forces are directed into a hoop stress which tends to radially expand the washer. This hoop stress is counterbalanced by the material strength of the washer, and the strain of the material causes a deflection in the height of the washer. Stated equivalently, a belleville washer responds to a compressive load by deflecting compressively, but provides a restoring force which is proportional to the elastic modulus of the material in a hoop stressed condition. With slots and/or grooves formed in the washer, it expands and restores itself far more elastically than a solid washer.

To dispose the spring mechanism between the plate members, the plate members of the artificial intervertebral disc comprise features suitable for this purpose. The spirally slotted and radially grooved belleville washer is utilized in conjunction with a ball-shaped protuberance on which it is free to rotate through a range of angles (thus permitting the plate members to rotate relative to one another through a corresponding range of angles). More particularly, one of the plate members has a circular recess on its interior surface, for housing the wide end of the belleville washer and allowing it to expand in unrestricted fashion when the belleville washer is compressed. The other of the plates has the ball-shaped protuberance on its interior surface, for rotatably holding the narrow end of the belleville washer. The protuberance has a central threaded axial bore that receives a rivet. Prior to the insertion of the rivet, the ball-shaped protuberance can deflect radially inward (so that the ball-shaped protuberance contracts). The insertion of the rivet eliminates the capacity for this deflection. The belleville washer is mounted to this ball-shaped knob in such a way that it may rotate freely through a range of angles equivalent to the fraction of normal human spine rotation (to mimic normal disc rotation). The belleville washer includes an enlarged inner circumferential portion (at the center of the washer) which accommodates the ball-shaped protuberance. The enlarged portion includes a curvate volume having a substantially constant radius of curvature which is also substantially equivalent to the radius of the ball-shaped protuberance. The deflectability of the ball-shaped protuberance, prior to the insertion of the rivet, permits the protuberance to be inserted into the interior volume at the center of the belleville washer. Subsequent introduction of the rivet into the axial bore of the protuberance prevents the protuberance from deflecting. Thereby, the washer can be secured to the ball-shaped protuberance so that it can rotate thereon through a range of angles.

This assembly provides spring-like performance with respect to axial compressive loads, as well as long cycle life to mimic the axial biomechanical performance of the normal human intervertebral disc. The spiral slots and radially extending grooves of the belleville washer allow the washer to expand radially as the slots and grooves widen under the load, only to spring back into its undeflected shape upon the unloading of the spring. As the washer compresses and decompresses, the walls of the circular recess maintain the wide end of the washer within a prescribed boundary on the internal face of the base plate which it contacts. The assembly further withstands tension loads on the vertebral body contact surfaces, because the rivet in the axial bore prevents the protuberance from deflecting, thus preventing the protuberance from exiting the curvate volume at the center of the belleville washer when the artificial intervertebral disc is under a tension load. Accordingly, once the plate members are secured to the vertebral bones, the assembly will not come apart when a normally experienced tension load is applied to the spine, similar to the tension-bearing integrity of a health natural intervertebral disc. The assembly further provides a centroid of motion centrally located within the intervertebral space, because the plate members are made angulatable relative to one another by the ball-shaped protuberance being rotatably coupled in the curvate volume of the enlarged portion of the belleville washer. The centroid of motion remains in the protuberance, and this remains centrally located between the vertebral bodies, similar to the centroid of motion in a healthy natural intervertebral disc.

DETAILED DESCRIPTION OF THE PREFERRED EMBODIMENT

Figure 1:
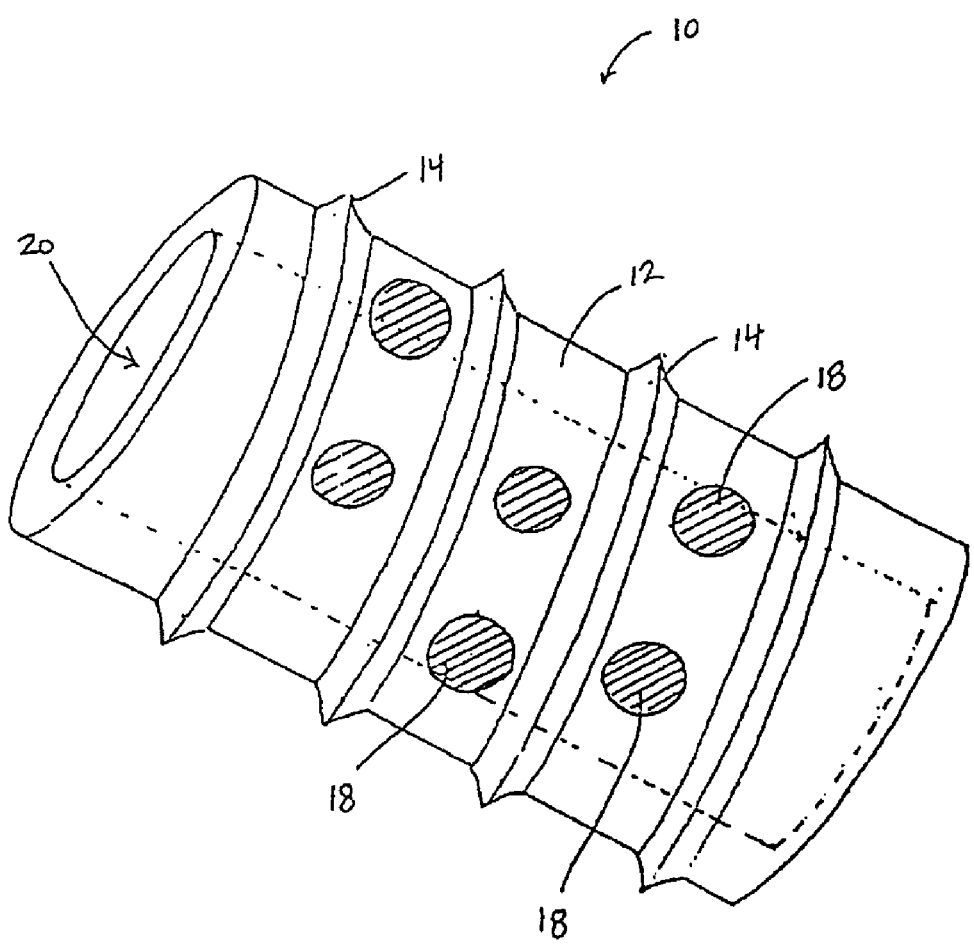
FIG. 1 is a side perspective view of an interbody fusion device of the prior art.
Figure 2:
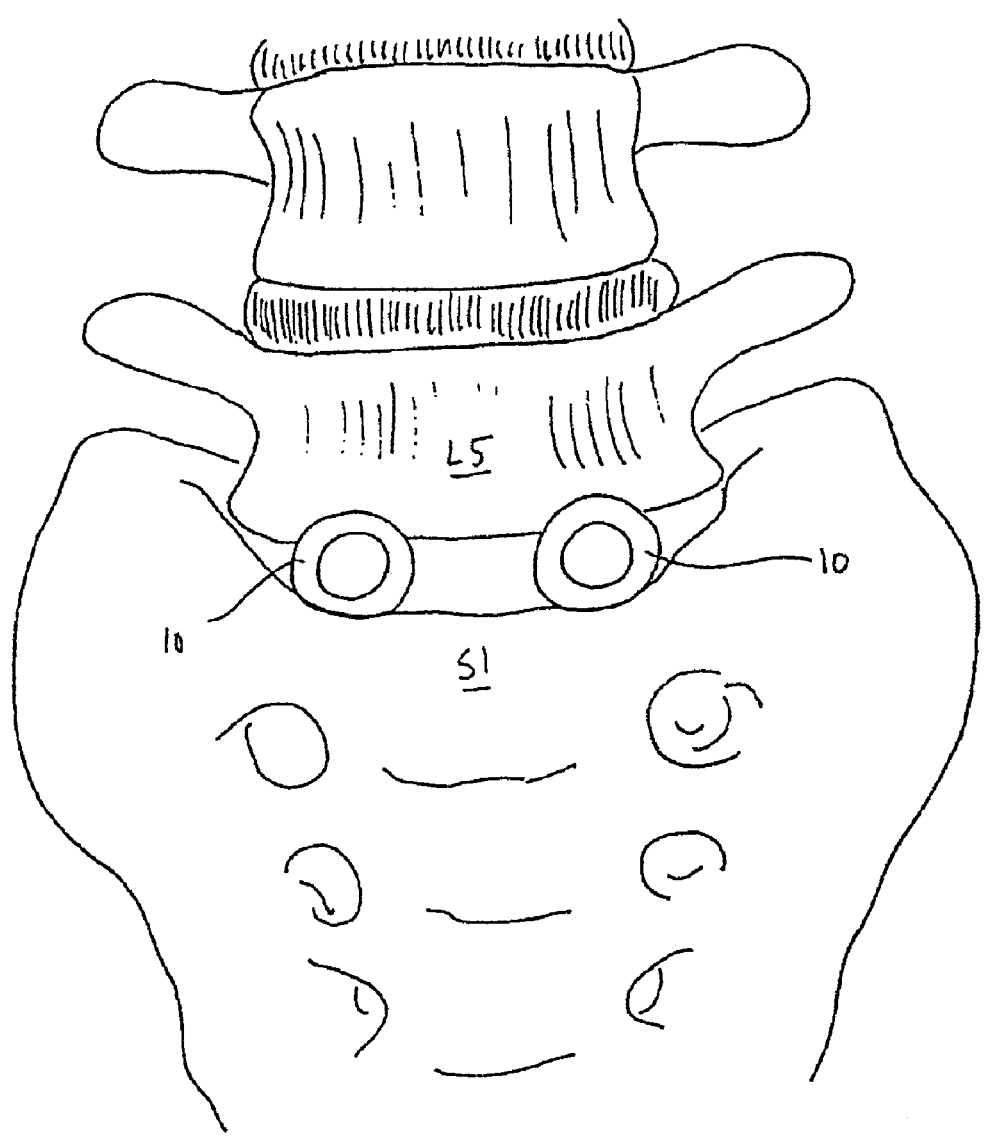
FIG. 2 is a front view of the anterior portion of the lumbosacral region of a human spine, into which a pair of interbody fusion devices of the type shown in FIG. 1 have been implanted.
Figure 3A:
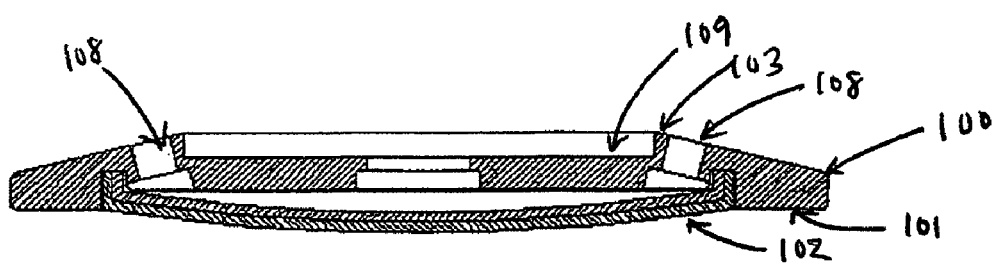
FIGS. 3a and 3b are side cross-section and top views of a lower plate member of an embodiment of the present invention.
Figure 3B:
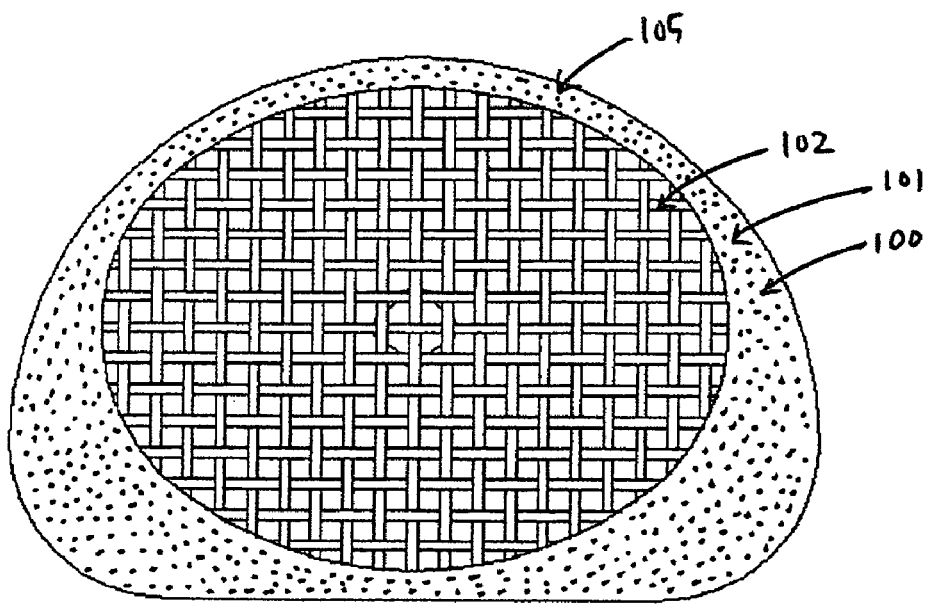
Figure 4:
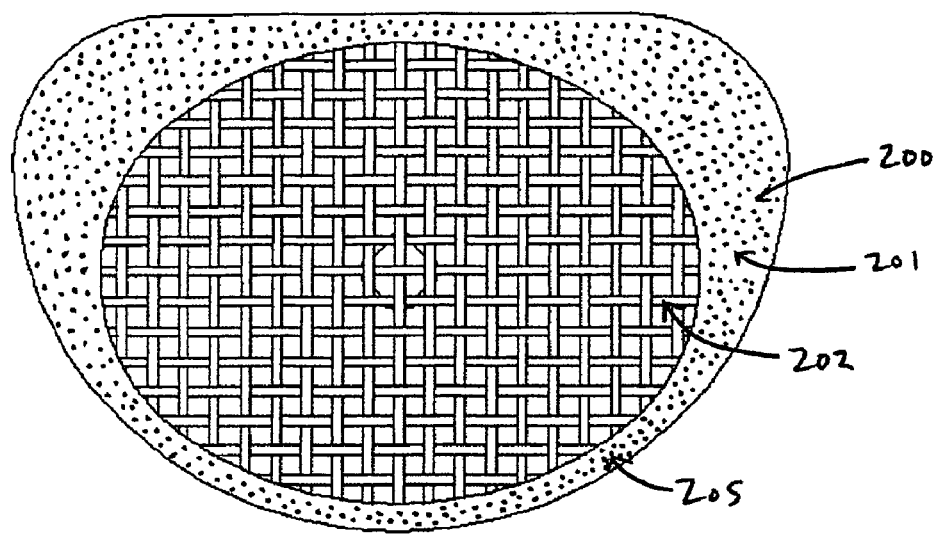
FIGS. 4a and 4b are side cross-section and top views of an upper plate member of an embodiment of the present invention.
Figure 4A:
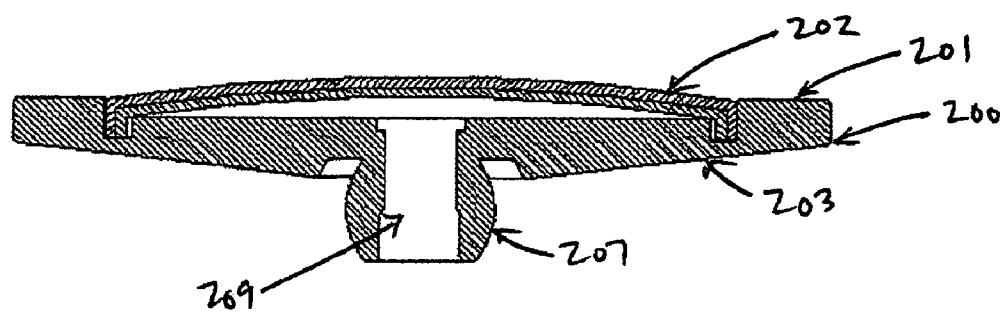

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the present invention and not as limiting of such broad scope. Like numbers refer to similar features of like elements throughout.

Referring now to FIGS. 3a, 3b, 4a and 4b, side cross-section and top views of lower and upper plate members 100,200 of an artificial intervertebral disc of the present invention are shown, each of the plate members 100,200 having a vertebral body contact surface 102,202. Because the disc is to be positioned between the facing surfaces of adjacent vertebral bodies, the plate members 100,200 are disposed such that the vertebral body contact surfaces 102,202 face away from one another as shown. The plate members 100,200 are to mate with the vertebral bodies so as to not rotate relative thereto, but rather to permit the spinal segments to axially compress and bend relative to one another in manners that mimic the natural motion of the spinal segment. This motion is permitted by the performance of a spring member (described in greater detail below) disposed between the secured plates 100,200. The mating of the plate members 100,200 to the vertebral bodies is described below.

More particularly, each plate member 100,200 is a flat metal plate having an overall shape that conforms to the overall shape of the respective bone endplate of the vertebral body with which it is to mate. Each plate member 100, 200 includes a peripheral region 100A, 200A extending about the outer region of the respective flat metal plate. Further, each plate member 100,200 comprises an oval convex metal mesh 102,202 that is attached to the exterior surface 101,201 of the plate member 100,200. The convex metal mesh 102,202 is secured at its perimeter, by laser welds, to the exterior surface 101,201 of the respective plate member 100,200. The metal mesh 102,202 is domed in its initial undeflected conformation, but deflects as necessary during insertion of the artificial intervertebral disc between vertebral bodies, and, once the artificial intervertebral disc is seated between the vertebral bodies, deforms as necessary under anatomical loads to reshape itself to the concave surface of the vertebral endplate. This affords the plate member 100,200 having the metal mesh 102,202 substantially superior gripping and holding strength upon initial implantation as compared with other artificial disc products. The convex metal mesh 102,202 further provides an osteoconductive surface through which the bone may ultimately grow. The mesh is preferably comprised of titanium, but can also be formed from other metals and/or non-metals without departing from the scope of the present invention.

In addition to the metal mesh 102,202, each plate member 100,200 further comprises at least a lateral ring 105,205 of porous coating (which may be a sprayed deposition layer, or an adhesive applied beaded metal layer, or other suitable porous coatings known in the art). This porous ring 105,205 permits the long-term ingrowth of vertebral bone into the plate member 100,200, thus permanently securing the prosthesis within the intervertebral space. It shall be understood that this porous layer 105,205 may extend beneath the domed metal mesh 102,202 as well, but is more importantly applied to the lateral rim of the exterior surface 101,201 of the plate member 100,200 that seats directly against the vertebral body.

It should be understood that the wire mesh attachment devices and methods described herein can be used not only with the artificial intervertebral discs and artificial intervertebral disc endplates described or referred to herein, but also with other artificial intervertebral discs and artificial intervertebral disc endplates, including those currently known in the art. Therefore, the description of the wire mesh attachment devices and methods being used with the artificial intervertebral discs and artificial intervertebral disc endplates described or referred to herein should not be construed as limiting the application and/or usefulness of the wire mesh attachment device.

With regard to the disposition of a spring member between the two plate members 100,200, the plate members 100,200 each comprise features for coupling the spring member (described below) therebetween (as described below). More specifically, the lower plate member 100 includes an internal face 103 that includes a circular recess 109 and a pair of holes 108 though which rivets 104 (shown in FIGS. 6 and 7) may be provided for securing a shield 250 (more fully set forth hereinbelow with and shown on FIG. 6). The upper plate member 200 includes an internal face 203 that includes a central interiorly directed ball-shaped protuberance 207. The protuberance 207 includes a series of slots 208 (shown on FIG. 6) that render the protuberance 207 radially compressible and expandable in correspondence with a radial pressure (or a radial component of a pressure applied thereto). The protuberance 207 further includes a central threaded axial bore 209 that is designed to receive a rivet 210 (shown in FIGS. 6 and 7). Prior to the insertion of the rivet 210, the protuberance 207 can deflect radially inward because the slots 208 will narrow under radial pressure. The insertion of the rivet 210 eliminates the capacity for this deflection. Therefore, the protuberance 207, before receiving the rivet 210, can be compressed to seat in the socket portion of the spring member (as described below), and, once the protuberance 207 has been seated in the socket portion, the rivet 210 can be inserted into the axial bore 209 to ensure that the protuberance 207 remains bald in the socket portion. A hole can be provided in the lower plate member 100 so that the interior of the device may be readily accessed if a need should arise.

Figure 5A:
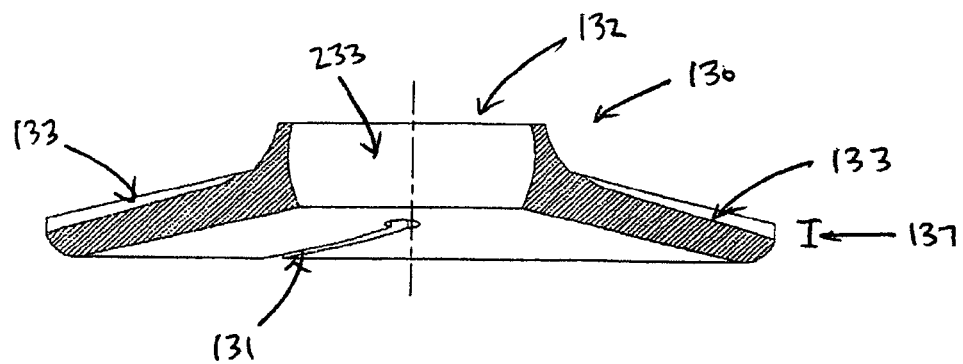
FIGS. 5a and 5b are side cross-section and perspective views of a belleville washer having radially extending grooves and spiral slots, for use with the present invention.
Figure 5B:
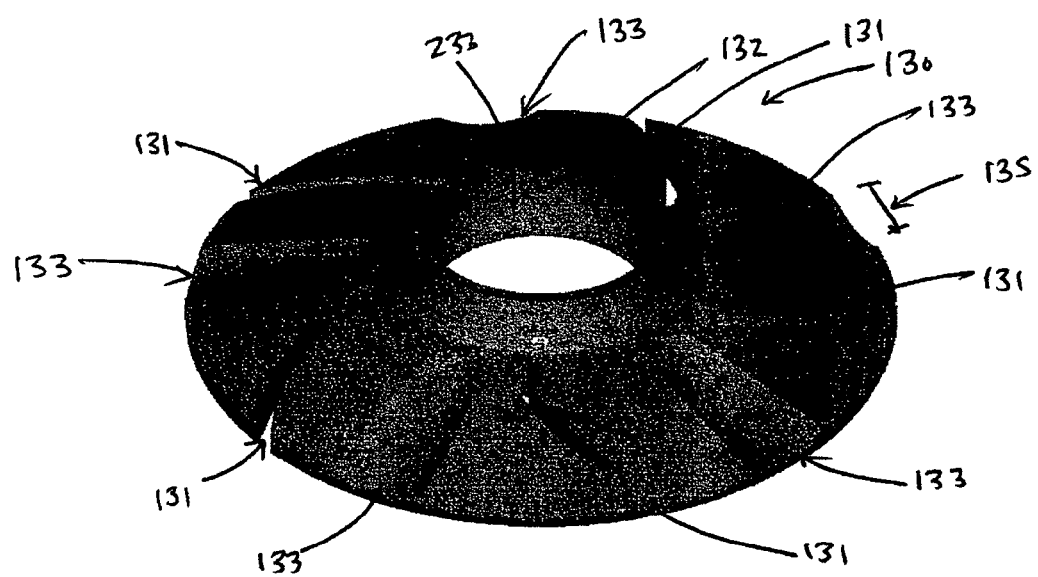

Referring now to FIGS. 5a and 5b, a spring member 130 for disposition between the plate members 100,200 is shown in side cross-section and perspective views as a spirally slotted belleville washer 130 having radially extending grooves. The belleville washer 130 is a restoring force providing device which comprises a circular shape, having a central opening 132, and which is radially arched in shape. The belleville washer 130 has a radial convexity (i.e., the height of the washer 130 is not linearly related to the radial distance, but may, for example, be parabolic in shape). The restoring force of the belleville washer 130 is proportional to the elastic properties of the material. It should be understood that belleville washers can be used with the present invention, and that belleville washers having other conformations, that is, without or without slots and/or grooves, and/or with other groove and slots configurations, including the same or different numbers of grooves and/or slots, are encompassed by the present invention.

The belleville washer 130 comprises a series of spiral slots 131 formed therein. The slots 131 extend from the outer edge of the belleville washer 130, inward along arcs generally directed toward the center of the element. The slots 131 do not extend fully to the center of the element. Preferably, the slots 131 extend anywhere from a quarter to three quarters of the overall radius of the washer 130, depending upon the requirements of the patient, and the anatomical requirements of the device.

The belleville washer 130 further comprises a series of grooves 133 formed therein. The grooves 133 extend radially from the outer edge of the belleville washer 130 toward the center of the element. Preferably, the width 135 and depth 137 of each groove 133 decreases along the length of the groove 133 from the outer edge of the washer 130 toward the center of the washer 130, such that the center of the washer 130 is flat, while the outer edge of the washer 130 has grooves of a maximum groove depth. It should be understood that in other embodiments, one or both of the depth and the width of each groove can be (1) increasing along the length of the groove from the outer edge of the washer toward the center of the washer, (2) uniform along the length of the groove from the outer edge of the washer toward the center of the washer, or (3) varied along the length of each groove from the outer edge of the washer toward the center of the washer, either randomly or according to a pattern. Moreover, in other embodiments, it can be the case that each groove is not formed similarly to one or more other grooves, but rather one or more grooves are formed in any of the above-mentioned fashions, while one or more other grooves are formed in another of the above-mentioned fashions or other fashions. It should be clear that any groove pattern can be implemented without departing from the scope of the present invention.

As a compressive load is applied to the belleville washer 130, the forces are directed into a hoop stress which tends to radially expand the washer 130. This hoop stress is counterbalanced by the material strength of the washer 130, and the force necessary to widen the spiral slots 131 and the radial grooves 133 along with the strain of the material causes a deflection in the height of the washer 130. Stated equivalently, the belleville washer 130 responds to a compressive load by deflecting compressively; the spiral slots and/or radial grooves cause the washer to further respond to the load by spreading as the slots and/or the grooves in the washer expand under the load. The spring, therefore, provides a restoring force which is proportional to the elastic modulus of the material in a hoop stressed condition.

With regard to the above discussion regarding the socket portion of the spring member, the socket portion is provided inasmuch as the central opening 132 of the belleville washer 130 is enlarged. This central opening 132 includes a curvate volume 233 for receiving therein the ball-shaped protuberance 207 of the upper plate 200. More particularly, the curvate volume 233 has a substantially constant radius of curvature which is also substantially equivalent to the radius of the ball-shaped protuberance 207. In this embodiment, the spiral slots 131 of the washer 130 do not extend all the way to the central opening 132, and approach the opening 132 only as far as the material strength of the washer 130 can handle without plastically deforming under the expected anatomical loading. Further in this embodiment, the depth 137 of each groove 133 of the washer 130 decreases along the length of the groove 133 from the outer edge of the washer 130 toward the center of the washer 130, such that the center of the washer 130 is flat, while the outer edge of the washer 130 has grooves of a maximum groove depth. Therefore, the central opening 132 can be formed from flat edges. It should be understood that this is not required, but rather is preferred for this embodiment.

Figure 6:
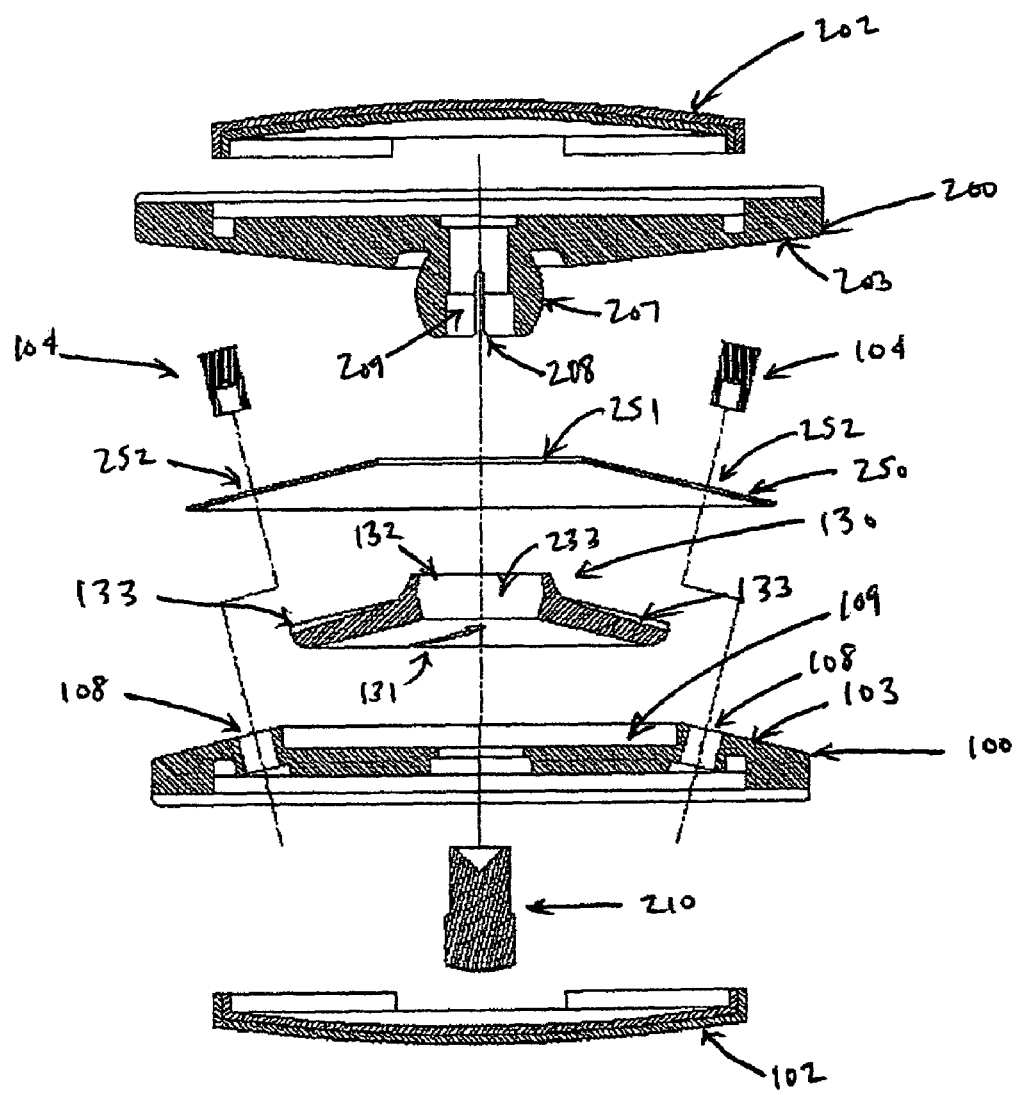
FIG. 6 is an exploded view of an embodiment of the present invention, utilizing the lower and upper plate members of FIGS. 3a, 3b, 4a and 4b and the belleville washer of FIGS. 5a and 5b.
Figure 7:
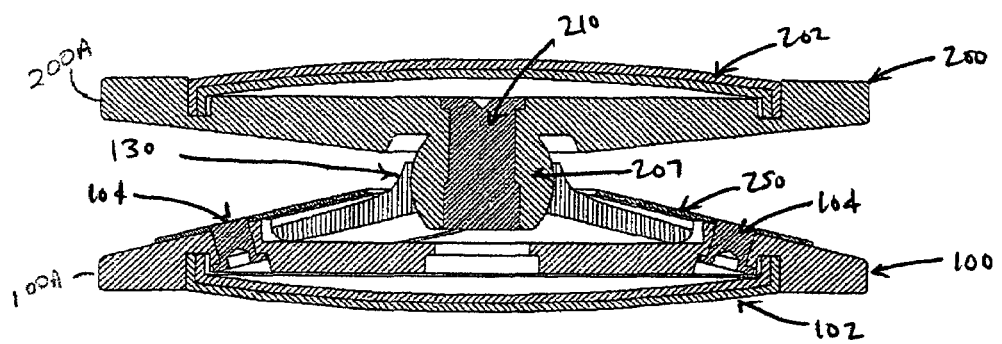
FIG. 7 is an assembled view of the embodiment of the present invention shown in FIG. 6.

Referring now to FIGS. 6 and 7, exploded and assembled views of the artificial intervertebral disc of the present invention is shown. Included in these views are the shield 250 and the corresponding rivets 104. More particularly, the device comprises a first plate member 200, having an upper, exterior, surface 201 and a lower interior surface 203 angled with respect to exterior surface 201, said upper, exterior surface 201 including a portion 205 thereof which is a porous, and a convex wire mesh 202. Peripheral region or first side surface 200A is formed between the exterior surface 201 and the interior surface 203. The lower, interior surface 203 includes a ball-shaped protuberance 207 extending out therefrom, said ball-shaped protuberance 207 including slits 208 and an axial bore 209 therein for permitting it to deflect inward under a compressive load. A rivet 210 is provided for selective insertion into said axial bore 209 of said ball-shaped protuberance 207 for inhibiting said inward deflection of the slits 208 once it has been inserted into the socket 233. A second plate member 100, disposed in parallel with said first plate 200 also has an upper, interior, surface 103 including a circular recess 109 formed therein, and a lower, exterior surface 101, wherein the interior, surface 103 is angled with respect to exterior surface 101, the exterior surface 101 having a portion 105 which includes a porous coating and a convex mesh 102. Peripheral region or second side surface 100A is formed between the exterior surface 101 and the interior surface 103.

The belleville washer 130 described above is shown with the ball-shaped socket 233 of its central opening 132 portion including a ball-shaped socket 233 for receiving and retaining therein the ball-shaped protuberance 207 of the first plate 200. When the wide end of the belleville washer 130 is seated in the circular recess 109, the shield 250 can be secured over the washer 130 by passing the central hole 251 of the shield 250 over the central opening 132 and applying the rivets 104 through rivet holes 252 in the shield 250 and through the rivet holes 108 in the lower plate 100. Thereafter, the protuberance 207 can be compressed into and thereby received in the socket 233 and the rivet 210 can then be received in the axial bore 209 to prevent the protuberance 207 from thereafter exiting the socket 233. When the protuberance 207 is in the socket 233, the belleville washer 130 can rotate and angulate on the protuberance to permit normal anatomical rotation and angulation. Further, because the diameter of the circular recess 109 is greater than the diameter of the wide end of the belleville washer 130, compressive loading of the device (and therefore the washer) can result in an unrestrained radial deflection of the washer 130, as necessary for proper anatomical response. The spiral slots 131 and radial grooves 133 of the washer 130 enhance this deflection. When the load is removed, the washer 130 springs back to its original shape.

Further, because the protuberance 207 is held within the socket 233 by the rivet 210 in the axial bore 209 preventing radial compression of the protuberance 207, the artificial intervertebral disc can withstand tension loading of the plate members 100,200, as necessary for proper anatomical response. More particularly, when a tension load is applied to the plate members 100,200, the ball-shaped protuberance 207 in the ball-shaped socket 233 of the belleville washer 130 seeks to radially compress to fit through the central opening 132 of the ball-shaped socket 233. However, the rivet 210 in the axial bore 209 of the protuberance 207 prevents the radial compression, thereby preventing the protuberance 207 from exiting the socket 233. Further, as the wide end of the belleville washer 130 seeks to escape the circular recess 109 of the lower plate member 100, the rivets 104 holding the shield 250 in place over the belleville washer 130 prevent the shield 250 from separating from the lower plate member 100 when the belleville washer 130 presses against the inner surface of the shield 250. Therefore, the assembly does not come apart under normally experienced tension loads. This ensures that no individual parts of the assembly will pop out or slip out from between the vertebral bodies when the patient stretches or hangs while exercising or performing other activities. Thus, in combination with the securing of the plate members 100,200 to the adjacent vertebral bones via the wire mesh domes 102,202, the disc assembly has an integrity similar to the tension-bearing integrity of a healthy natural intervertebral disc.

Further, because the plate members 100,200 are made angulatable relative to one another by the ball-shaped protuberance 207 being rotatably coupled in the socket 233 of the belleville washer 130, the disc assembly provides a centroid of motion within the protuberance 207. Accordingly, the centroid of motion of the disc assembly remains centrally located between the vertebral bodies, similar to the centroid of motion in a healthy natural intervertebral disc.

While there has been described and illustrated specific embodiments of an intervertebral spacer device, it will be apparent to those skilled in the art that variations and modifications are possible without deviating from the broad spirit and principle of the present invention. The invention, therefore, shall not be limited to the specific embodiments discussed herein.

What is claimed is:

1. An artificial intervertebral disc, comprising:
a first member having a first exterior vertebral body contact surface, a first inner surface angled with respect to the first exterior vertebral body contact surface, and a first side surface formed between the first exterior vertebral body contact surface and the first inner surface;
a second member having a second exterior vertebral body contact surface, a second inner surface angled with respect to the second exterior vertebral body contact surface, and a second side surface formed between the second exterior vertebral body contact surface and the second inner surface, the first and second members being disposed such that the vertebral body contact surfaces face away from one another; and
a coupling by which the first and second members are coupled to one another such that the first and second vertebral body contact surfaces are angulatable relative to one another about a centroid of motion centrally located between the first and second vertebral body contact surfaces, the coupling including a protrusion having a semi-spherical surface with at least one slot therein and a restoring force providing element seated in a circular recess formed in one of the inner surfaces of the first and second members, the restoring force providing element having a curvate socket wherein the semi-spherical surface of the protrusion only fits through and becomes seated in the curvate socket when radially compressed such that the at least one slot narrows; and a shield coupled to the second plate and overlying the circular recess such that the restoring force providing element is captured within the circular recess, wherein no structure contacts the side surfaces of the first and second members during angulation of the first and second members relative to one another.

2. The artificial intervertebral disc of claim 1, wherein the protrusion is a ball.

3. The artificial intervertebral disc of claim 2, wherein the ball and curvate socket include a radially compressible ball, the curvate socket having an interior volume and a mouth leading to the interior volume, the curvate socket accommodating the ball for free rotation therein, the ball being adapted to receive a radial compression preventing element that when applied to the ball prevents the ball from fitting through the mouth.

4. The artificial intervertebral disc of claim 3, wherein the ball has an axial bore and the radial compression preventing element comprises a set screw that is receivable by the bore.

5. The artificial intervertebral disc of claim 1, wherein the restoring force providing element is rotatable on the protrusion.

6. The artificial intervertebral disc of claim 5, wherein the restoring force providing element comprises a belleville washer.

7. The artificial intervertebral disc of claim 6, wherein the belleville washer has at least one slot.

8. The artificial intervertebral disc of claim 6, wherein the belleville washer has at least one groove.

9. The artificial intervertebral disc of claim 1, wherein the first member includes the protrusion and the second member includes at least one retaining element by which the restoring force providing element is maintained adjacent the second member under a tension load.

* * * * *